(12) United States Patent
Borwick, III et al.

(10) Patent No.: US 7,287,415 B2
(45) Date of Patent: Oct. 30, 2007

(54) MICROELECTROMECHANICAL SYSTEM (MEMS) VISCOSITY SENSOR FOR FLUID HEALTH MONITORING

(75) Inventors: Robert L. Borwick, III, Thousand Oaks, CA (US); Philip A. Stupar, Oxnard, CA (US); Jeffrey F. DeNatale, Thousand Oaks, CA (US)

(73) Assignee: Teledyne Licensing, LLC, Thousand Oaks, CA (US)

( * ) Notice: Subject to any disclaimer, the term of this patent is extended or adjusted under 35 U.S.C. 154(b) by 53 days.

(21) Appl. No.: 10/956,229

(22) Filed: Sep. 30, 2004

(65) Prior Publication Data

US 2006/0065045 A1 Mar. 30, 2006

(51) Int. Cl.
*G01N 11/00* (2006.01)
(52) U.S. Cl. .................................................. 73/54.01
(58) Field of Classification Search ................. 73/54.01
See application file for complete search history.

(56) References Cited

U.S. PATENT DOCUMENTS

| | | | | |
|---|---|---|---|---|
| 2,679,750 A * | 6/1954 | Brookfield | ................. | 73/54.33 |
| 2,865,197 A * | 12/1958 | Penther et al. | ............. | 73/54.22 |
| 4,878,013 A * | 10/1989 | Andermo | ................... | 324/690 |
| 4,879,552 A * | 11/1989 | Arai et al. | ............. | 340/870.37 |
| 5,199,298 A * | 4/1993 | Ng et al. | .................... | 73/54.01 |
| 5,726,581 A * | 3/1998 | Vranish | ....................... | 324/688 |
| 5,955,659 A | 9/1999 | Gupta et al. | .................... | 73/54 |
| 6,159,385 A | 12/2000 | Yao et al. | ....................... | 216/2 |
| 6,644,101 B2 * | 11/2003 | Hajduk et al. | ............. | 73/54.37 |
| 6,668,622 B2 * | 12/2003 | Hajduk et al. | ............. | 73/54.37 |
| 7,036,372 B2 * | 5/2006 | Chojnacki et al. | ........ | 73/504.12 |
| 7,047,794 B2 * | 5/2006 | Hajduk et al. | ............. | 73/54.37 |
| 2005/0066728 A1* | 3/2005 | Chojnacki et al. | ........ | 73/514.16 |
| 2006/0027738 A1* | 2/2006 | Berting et al. | ......... | 250/231.13 |

* cited by examiner

*Primary Examiner*—Hezron Williams
*Assistant Examiner*—John Fitzgerald
(74) *Attorney, Agent, or Firm*—Koppel, Patrick, Heybl & Dawson

(57) ABSTRACT

Embodiments of the present invention are directed to a MEM viscosity sensor that is configured to be operated submerged in a liquid. The MEMS viscosity sensor comprises a MEMS variable capacitor comprising a plurality of capacitor plates capable of being submerged in a liquid. An actuator places a driving force on the variable capacitor which causes relative movement between the plates, where the movement creates a shear force between each moving plate and the liquid, which damps the movement of the plate and increases the capacitor's response time to the applied force in accordance with the liquid's viscosity. To determine the actual viscosity of the liquid, a sensor is coupled to the variable capacitor for sensing the response time of the plates as an indicator of the liquid's viscosity.

24 Claims, 5 Drawing Sheets

MICROELECTROMECHANICAL SYSTEM (MEMS) VISCOSITY SENSOR FOR FLUID HEALTH MONITORING

FIELD OF THE INVENTION

The present invention is directed to a microelectromechanical system (MEMS) and in particular, to a device having a plurality of plates for measuring fluid viscosity.

BACKGROUND OF THE INVENTION

Many mechanical systems, such as vehicles, require liquids for their operation. To extend the life of the equipment, such liquids must be maintained, including the replacement of spent and degraded liquids.

Most systems are maintained on a scheduled basis, which is not dependent upon the actual condition of the liquid, but rather, is based upon the general understanding of the liquid's life. For example, most drivers change the oil in their vehicles at predefined mileage intervals, such as every 3000 miles. Although this is beneficial, it fails to account for other factors that may affect the condition of the liquid. For example, a failure in the equipment could cause the liquid to degrade at a faster rate than that anticipated by the normal replacement schedule. Similarly, the condition of the equipment might be such that the liquid's useful life is extended. Thus, costs can be increased due to poorly operating equipment or due to unnecessary liquid replacement. If the equipment requiring maintenance is a fleet, the expense could be quite large.

Currently, electrochemical sensor systems exist that allow the monitoring and measurement of the condition, or health, of such liquids. Indeed, many monitoring systems exist which measure a variety of liquid parameters, including, dielectric constant, conductivity, pH and the amount of water in the liquid. Although such measurements are useful, taken in isolation they do not necessarily identify the health of the liquid unless the user is also aware of the measurement's history. For example, if the value of a particular parameter rises or falls as the liquid degrades, the liquid's health would be unclear from a single measurement. Rather, the parameter's history would be required to accurately assess the liquid condition.

One solution to the problems presented by electrochemical measurements is to measure liquid viscosity that, by itself, can be a good indicator of liquid health. The measurement of viscosity does not suffer from the historical problems associated with electrochemically measured parameters of the liquid. Indeed, if viscosity increases monotonically with operating time and, if a liquid's viscosity degradation profile is known in advance, then its health can be determined by a single measurement regardless of when the measurement is taken.

As viscosity is not directly measured by electrochemical sensors, but rather, is measured by the application of mechanical forces, including compressive forces and shear forces, a separate measuring sensor must be used. One approach uses a vibrating quartz or piezoelectric element that measures the shift in a device's resonant frequencies in response to applied vibrations, which in turn is a measurement of the damping value Q and thus of viscosity. The measurement of Q, however, is not a linear measurement, and thus will not be useful for a wide viscosity range.

Further, this manner of measuring viscosity introduces complexities because it applies both compressive and shear forces. The contributions of both components to the net response can complicate data interpretation and limit operating range.

A more desirable and accurate viscosity measurement is obtained with a shear force measurement. One shear force measurement technique involves the dropping of large balls through cylinders filled with the liquid to be measured. As the ball moves through the liquid, the shear force resulting between the moving balls and the liquid can be measured. Although this technique is accurate, it is not useful for smaller systems or equipment, and thus, is limited in its applications.

As seen from above, although viscosity measurements are desirable, current liquid monitoring systems require separate electrochemical and viscosity sensors to monitor both liquid health, and also the other liquid characteristics available from an electrochemical sensor. Indeed, most users will not simply replace their electrochemical sensors and rely solely on a viscosity measurement.

A need in the industry exists for a measurement system that provides the ability to measure the health of a liquid in a system, wherein the measuring system resides within the system. A further need in the industry exists for a viscosity sensor that utilizes a shear force measurement technique that can be used in small or confined environments, and can be combined with other sensors.

SUMMARY OF THE DISCLOSURE

Embodiments of the present invention are directed to a MEM viscosity sensor that is configured to be operated submerged in a liquid. The MEMS viscosity sensor comprises a MEMS variable capacitor comprising a plurality of capacitor plates capable of being submerged in a liquid. An actuator places a driving force on the variable capacitor which causes relative movement between the plates, where the movement creates a shear force between each moving plate and the liquid, which opposes the movement of the plate and increases the capacitor's response time to the applied force in accordance with the liquid's viscosity. To determine the actual viscosity of the liquid, a sensor is coupled to the variable capacitor for sensing the response time of the plates as an indicator of the liquid's viscosity. A feature of preferred embodiments is that the liquid sensor can be small in size. The sensor can thus be placed within a system for directly measuring the health of a system liquid on a continuous basis. It can also alert the user to equipment failure as it relates to the rate of degradation of the equipment liquid.

The MEMS structure allows for the integration of the sensor with other electronic circuits used for monitoring liquid health, while the bulk manufacturing of MEMS devices reduces costs.

Another feature of preferred embodiments is that a mechanical, thermal, electromagnetic, and chemical evaluation of liquids can be integrated into a single sensor, allowing the number and cost of separate sensors to be reduced, and multiple parameters measuring the health of a liquid to be monitored by a single component.

The preferred system measures viscosity via the application of a shear force, which reduces measurement errors and widens measurement ranges.

BRIEF DESCRIPTION OF THE DRAWINGS

The detailed description of embodiments of the invention will be made with reference to the accompanying drawings, wherein like numerals designate corresponding parts in the figures.

DETAILED DESCRIPTION OF THE PREFERRED EMBODIMENTS

Embodiments of the present invention are directed to a MEMS viscosity sensor 10 disposed on a supporting substrate 12. The viscosity sensor 10 is configured to directly measure the ability of the liquid to reduce friction. Fabrication techniques to create such a MEMS are known in the art and are described in U.S. Pat. No. 6,159,385, and U.S. patent application, entitled Microelectromechanical System (MEMS) Devices and Fabricating Methods, Ser. No. 10/454,031, filed on Jun. 2, 2003, which are fully incorporated herein by reference. In preferred embodiments, during use the MEMS viscosity sensor is submerged in a liquid. Use of a submersible MEMS device is described in pending application Ser. No. 10/227,141 entitled Liquid Medium Submerged MEMS Device, which is fully incorporated herein by reference.

Figure 1:
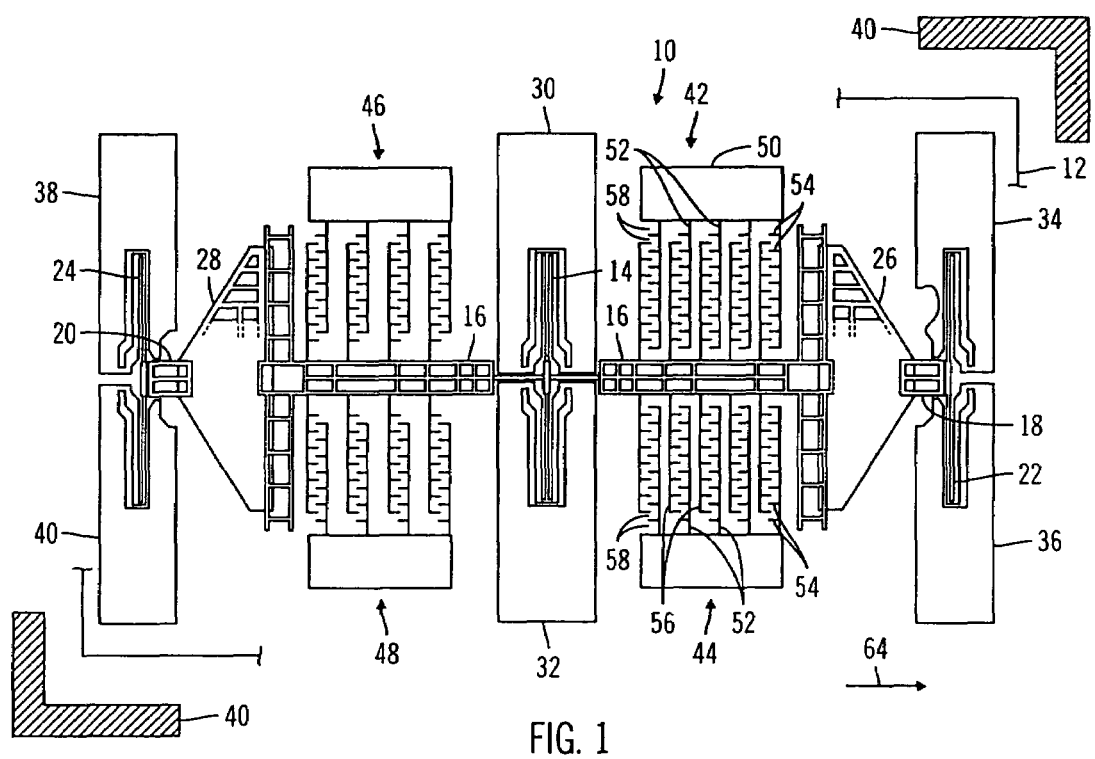
FIG. 1 is an elevation view of a viscosity sensor in accordance with a preferred embodiment of the invention.

With reference to FIG. 1, in one preferred embodiment, the viscosity sensor 10 comprises a transverse, centrally located, compliant suspension 14 carrying a longitudinally-extending arm 16. The arm 16 includes transverse ends 18 and 20 coupled to compliant, electrically conductive suspension beams 22 and 24, via electrically insulating bridges 26 and 28, respectively, fabricated of, for example, silicon dioxide. In preferred embodiments, the arm 16 and suspensions 14, 22 and 24 are mechanically coupled together to move longitudinally as a single unit with respect to the substrate 12, and form a motion actuator. The bridges 26 and 28, however, electrically isolate the arm 16 from the electrically conductive suspensions 22 and 24. The suspension 14 is coupled at its opposed outer ends to anchors 30 and 32 affixed to the substrate 12. Similarly, the outer ends of suspensions 22 and 24 are coupled to anchor pairs 34, 36 and 38, 40 respectively, affixed to the substrate 12.

The sensor 10 further comprises comb sense capacitors 42, 44, 46 and 48 (also known as interdigitated capacitors) for providing to an external output circuit signals representing the displacement of the arm 16 from its rest position. A pair of comb capacitors 42 and 44 straddle the arm 16 adjacent to the right end suspension 24. Similarly, a pair of comb capacitors 46 and 48 straddle the arm 16 adjacent to the left end suspension 22. Since the comb capacitors 42, 44, 46 and 48 are identical, only the right hand comb capacitor 42 will be described.

Figure 2:
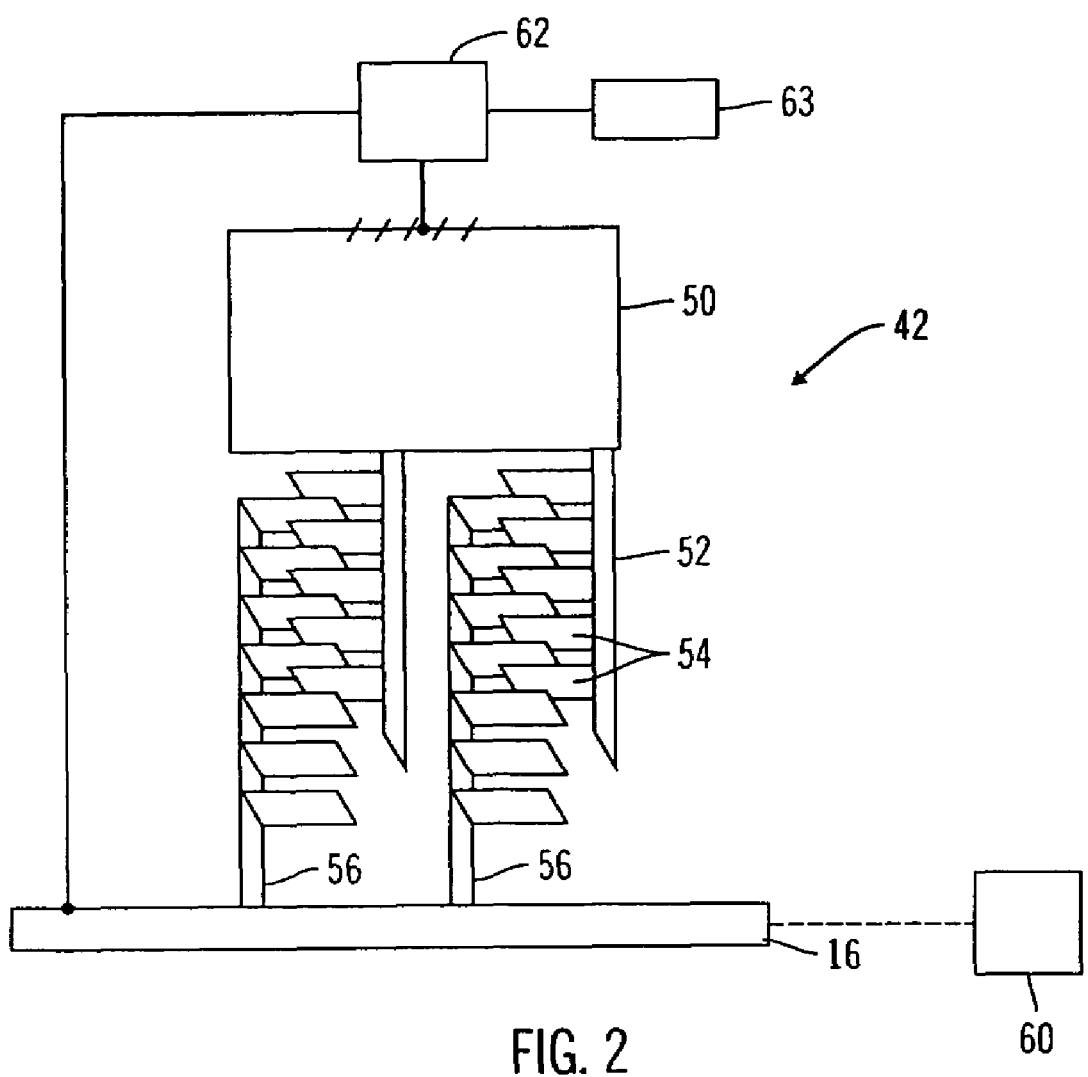
FIG. 2 is an elevation view of a comb capacitor having interdigitated plates in accordance with the embodiment of FIG. 1.

With reference to FIG. 2, the comb capacitor 42 comprises a fixed member 50 having a plurality of cantilevered support members 52. Comb fingers 54, also referred to as comb plates, extend longitudinally from the support member 52 to provide a large surface area for interacting with liquids. The capacitor 42 further comprises a plurality of connectors 56 cantilevered from the moveable arm 16. Comb fingers 58, also referred to as comb plates, extend longitudinally from connectors 56, and are configured to interleave with the comb plates 54. Similar to fixed comb plates 54, moveable comb plates 58 also provide a large surface area for interacting with liquids. The comb plates 54, 58 are made from electrically conductive materials, such as silicon on which metals or alloys may be coated or plated onto said plates. In preferred embodiments, the plates are thin enough to reduce or eliminate compressive forces that may be created by their movement through a medium, such as, a liquid. The fixed member 50, cantilevered support members 52, cantilevered connectors 56, and combination of the interleaved stationary and moveable comb plates 54 and 58, appropriately connected to a drive actuator 60, forms a variable capacitor whose capacitance varies with the amount of overlap between plates 54 and 58.

With further reference to FIG. 2, the sensor 10 is coupled to a drive actuator 60, a sensor 62 and a read-out 63, which are electrically coupled to the capacitor. In preferred embodiments, the drive actuator 60 can be an electrostatic actuator, or a Lorentz force actuator. Regardless of the type of drive actuator utilized, the drive actuator 60 causes transverse suspensions 22, 24 to move bridges 26, 28 longitudinally in the plane of FIG. 1 such that plates 54 move parallel to plates 58.

In preferred embodiments, either an electrostatic actuator or a Lorentz force actuator can be utilized to move the arm 16, and thus cause the comb plates 54 to move relative to the fixed comb plates 58 with which the plates 54 are interleaved. Alternate actuation methods such as thermal, electromagnetic, and piezoelectric may also be used as known to those skilled in the art. A description of electrostatic actuators suitable for use in embodiments of the invention are described in U.S. Pat. No. 5,025,346, entitled Electrostatic Comb Drive Actuator, which is incorporated herein by reference. A description of Lorentz force actuators suitable for use in embodiments of the invention are described in U.S. patent application Ser. No. 10/213,951, entitled A Lorentz Force Microelectromechanical System (MEMS) and A Method for Operating Such A MEMS, which is incorporated herein by reference. In one example with a Lorentz force actuator, a magnetic field source, such as a permanent magnet or electromagnet typically disposed above or below the substrate 12, provides a magnetic field. Connections to one or more external circuits are made via anchors 34, 36, 38 and 40 carrying the suspensions 22 and 24, to which the anchors are electrically connected. If current flows from a connected external circuit through the suspension 22, a Lorentz force causes the arm 16 and the moveable portions of the interconnected compliant suspensions 14, 22 and 24 to move laterally as indicated by the arrow 64 (FIG. 1). As the current flowing through one of the suspensions 22 varies, the distance that arm 16 moves varies, to vary the overlap between the comb plates 54, and 58, thus varying the capacitance between them.

If the capacitors are immersed in a liquid, the liquid will dampen the movement of the comb plates 54, 58 upon the application of the driving force from the drive actuator 60. The liquid has an initial viscosity value and a degraded viscosity value which may change as a function of operating time. The response time of the device, as determined through the capacitive sensing, provides a measure of the fluid viscosity. If the degraded viscosity value changes relative to the initial viscosity value there will be a corresponding change in time response. The measured response time will be related to the new viscosity value, which in turn, is related to the health of the liquid.

Figure 4:
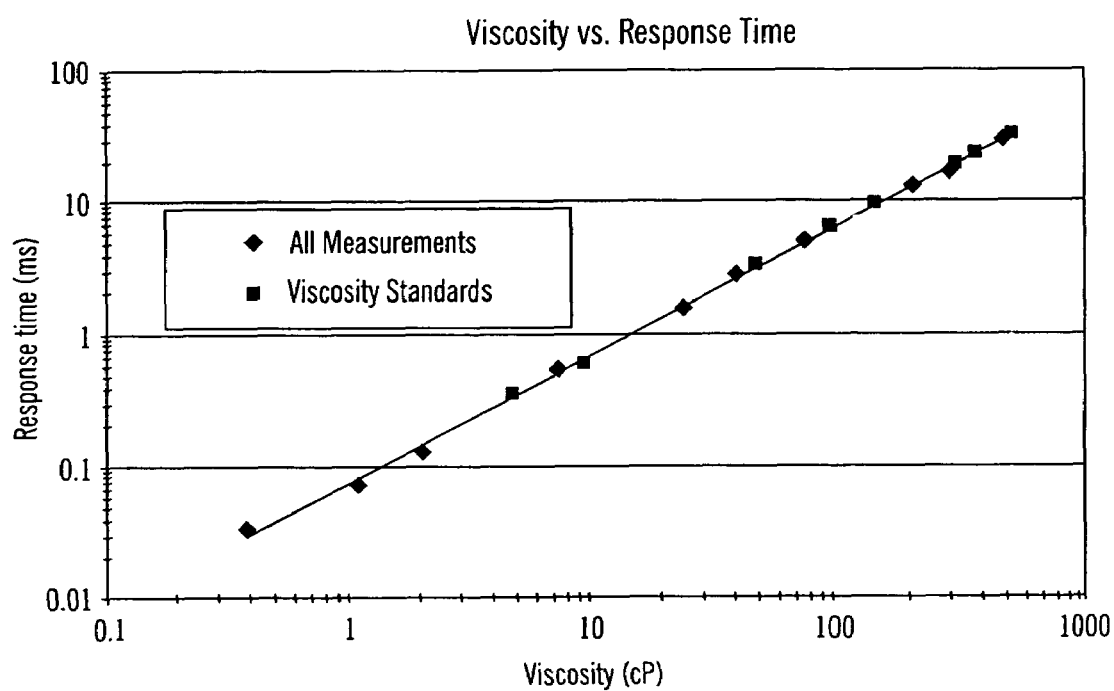
FIG. 4 is a graph depicting viscosity response time versus viscosity for various measured liquids.

By connecting the capacitors to a sensor 62 that may comprise, for example, a resonant circuit or a high frequency a.c. bridge, minute displacement of the comb plates 58 may be sensed capacitatively and converted into a voltage. The sensor 62 preferably includes a timing means for sensing the time for the comb plates 58 to move from, for example, 30% of the maximum displacement to, for example, 70% of the maximum displacement. The voltage and time is used to determine the response time of the comb plates 58, and thus, calculate a viscosity value. As shown in FIG. 4, such response time and viscosity of the liquid within which the sensor is immersed are related linearly as plotted along log/log axes. The viscosity may be displayed directly on a read-out 63. Any suitable device for displaying the viscosity can be used, including, but not limited to, a digital display.

The viscosity sensor 10 is configured in a manner which allows at least the comb capacitor 42 to be immersed in a liquid medium. For example, as shown in FIG. 1, a set of walls 40 extending from the substrate surrounds the sensor, allowing the liquid's health to be directly measured. The enclosure created by the walls 40 does not include a top and thus, the sensor is exposed. In this regard, liquid can fill inside the walls and cover the comb capacitors 42, 44. If the viscosity sensor 10 is submersed in liquid, the walls assist in reducing agitation of the liquid nearest the comb plates.

The configuration of the comb plates 54, 58 allow the viscosity to be measured via a shear force. Indeed, when immersed in a liquid, as the comb plates 54, 58 interleave due to the force applied by the drive actuator 60, a shear force between the liquid and the surface area of the movable comb plates 58 are created as the comb plates 58 move through the liquid. The more viscous the liquid, the more resistance is encountered by the comb plates 58 as they move through the liquid. Conversely, the less viscous the liquid, the less resistance is encountered by the comb plates 58 as they move through the liquid. Due to the configuration of the comb plates 54, 58 only a shear force is created by the movement of the movable comb plates 58 through the liquid, and thus, the viscosity measurement is more accurate as there are no compressive forces included in the measurement.

As the viscosity of a liquid affects the mechanical performance of a MEMS device, various measurements can be utilized to measure the viscosity of the liquid based upon the response of the MEMS device to an applied force. In preferred embodiments, a measurement of the damping force, that is, the amount of time which is required for the connectors 56 to cease moving in response to the applied force can be used to determine the viscosity of the liquid. To measure the damping force, the step response time or the resonant frequency shift is measured.

Figure 3:
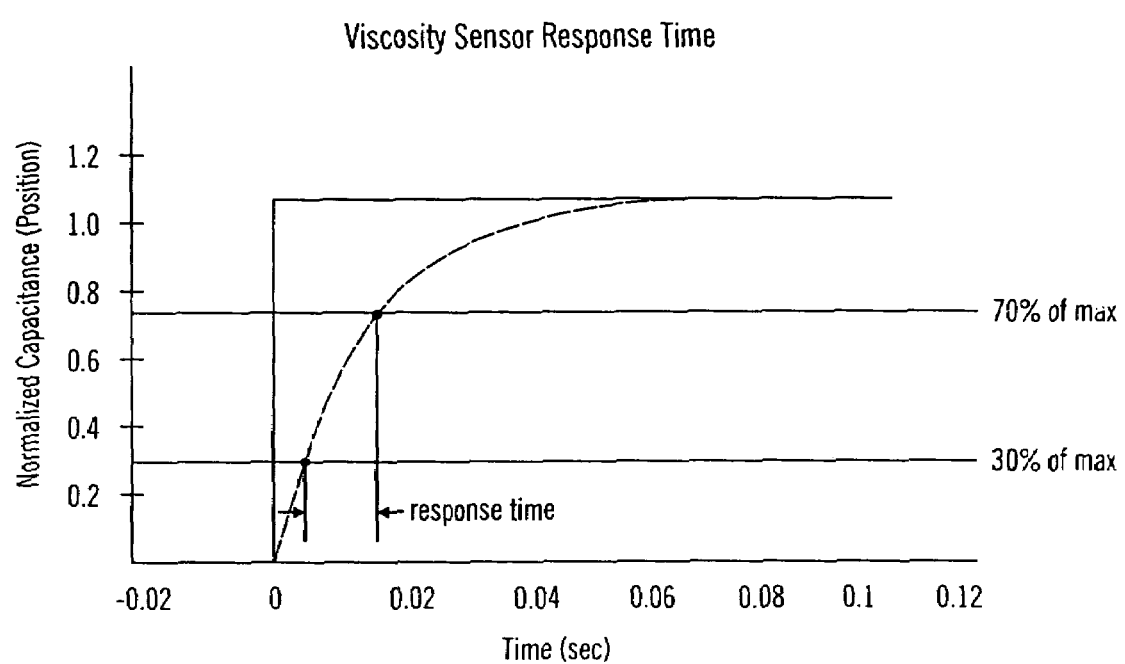
FIG. 3 is a graph of viscosity sensor response time.

FIG. 3 depicts an ideal step function representing the applied force. The graph depicts viscosity sensor response time, showing the capacitance, which is a function of position, versus time. In response to a step function input the ideal system instantaneously displaces a maximum value, which is normalized to 1. To determine the response times of various liquids, the response of a device submerged in a liquid to a step function is measured between two preset values, for example, between 30% and 70%. The results of the measurement of the viscosity for various liquids for the preset values are plotted in FIG. 4. FIG. 4 depicts the viscosity of the various measured liquids as determined by the response time against a viscosity standard (straight line).

Figure 5:
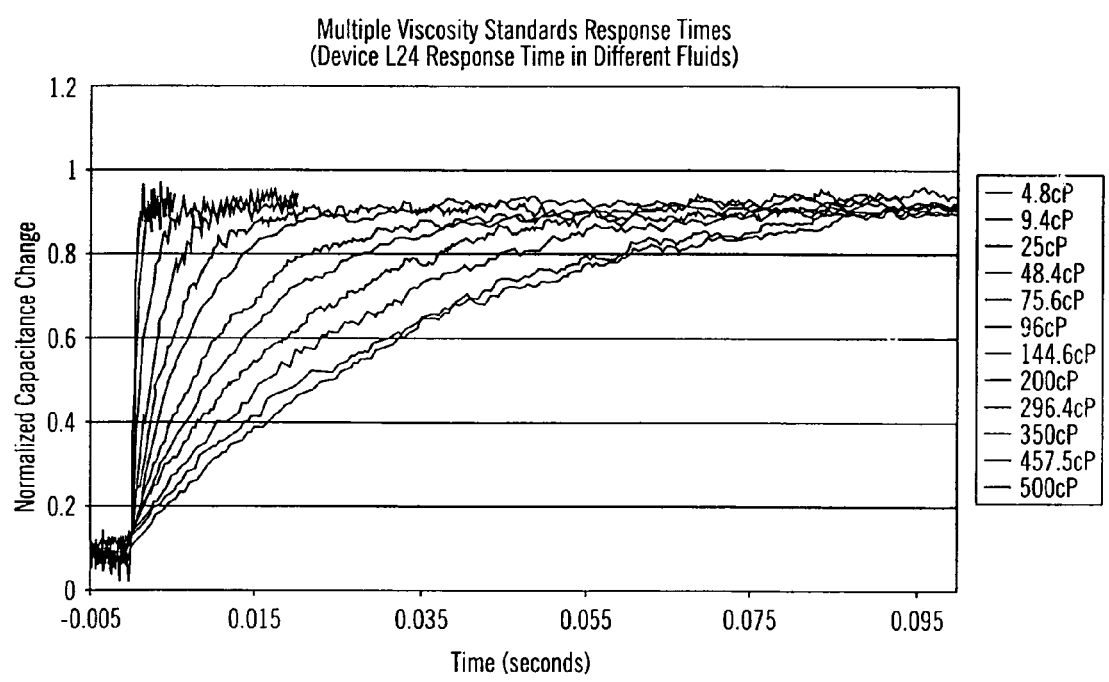
FIG. 5 is a graph depicting the response time of the various measured liquids of FIG. 4.

As shown in FIG. 4, there is a high linearity of response time and viscosity measurement. The health of the liquid can be determined based upon the measured value of viscosity, compared to the healthy viscosity profile for the given liquid being measured. In the described preferred embodiments of the invention, changes in viscosity of 1% can be detected by the sensor 10. FIG. 5 depicts the standard response times of a MEMS device as a graph of the MEMS capacitance change in various fluids versus time. As the over-damped step response time varies positively with viscosity, the viscosity of the fluid can be plotted against the response time. Each response time (traces) depicted in FIG. 5 represents a measurement of viscosity versus response time as plotted on FIG. 4.

Embodiments of the device can be utilized in a variety of situations in which measurements determining the health of a liquid are desired. For example, a sensor can be installed in the oil tank of a vehicle, machine, or in a separate testing apparatus to which liquid samples are brought. In operation, the drive actuator 60 causes a drive voltage to be applied to the suspensions 22, 24. Assuming a Lorentz force actuator as an example, if current flows from an external circuit through the suspensions, in the presence of a magnetic field, a Lorentz force causes the arm 16 and suspensions 14, 22 and 24 to move as a single unit with respect to the substrate 12. As the suspensions 14, 22 and 24 move, the arm 16 is linearly translated in the direction of arrow 64 (FIG. 1), which in turn moves the connectors 56 and moveable comb plates 58. This causes the comb plates 58 to interleave with the fixed comb plates 54, thereby causing a change in the displacement and, hence capacitance, between the comb plates 58. The change in the displacement of the comb plates 58, as well as the response time, is measured by the measurement element 62. The change in the displacement as a function of the response time allows the user to determine the viscosity of a liquid by correlating the response time of the measured displacement to known viscosity standards for the particular liquid and thus, to determine whether the measured liquid is healthy. A viscosity measurement which is based upon the displacement measurement of the comb plates is displayed in the read-out 63.

Although the foregoing described the invention with preferred embodiments, this is not intended to limit the invention. Indeed, embodiments of this invention can be combined with other sensors and systems, such as other lubrication health sensors. In other embodiments, the viscosity sensor can be directed integrated with a stationary interdigitated sensor where the interdigitated sensor is created on the same chip by the same fabrication process for electrochemical sensing. In some embodiments, a separate element, such as a separate thin plate, can be included in addition to a sensing capacitor where the thin plate is configured to move with respect to the substrate and produce a shear force which is measured by a sensor. In still other embodiments, the viscosity sensor can be combined with a temperature sensor which distinguishes degradation from temperature dependent viscosity changes. As seen from the foregoing, the embodiments of the viscosity sensor are intended to be used as a stand alone sensor or in combination with other types of sensors. In this regard, the foregoing is intended to cover all modifications and alternative constructions falling within the spirit and scope of the invention as expressed in the appended claims, wherein no portion of the disclosure is intended, expressly or implicitly, to be dedicated to the public domain if not set forth in the claims.

What is claimed is:

1. A micro-electromechanical system (MEMS) capable of being submerged in a liquid, comprising:
   a substrate;
   a capacitor comprising:
      first and second thin sets of conductive plates spaced apart from each other and having parallel respective surface areas, the first set of plates being configured to interleave with the second set of plates such that their surface areas at least partially overlap to produce a capacitance which varies with the amount of overlap, at least one of said sets of plates being moveable to vary said overlap, said surface of said plates providing predominantly shear interaction with said liquid; and
   a motion actuator carried by said substrate coupled to move said at least one set of plates.

2. The MEMS of claim 1, wherein said capacitor is a comb capacitor.

3. The MEMS of claim 1, further comprising a drive actuator, coupled to move at least one of said set of plates parallel to the other sets of plates to vary said overlap.

4. The MEMS of claim 3, wherein the drive actuator is a Lorentz actuator.

5. The MEMS of claim 3, wherein the drive actuator is an electrostatic actuator.

6. The MEMS of claim 3, wherein the drive actuator is selected from a group consisting of an electromagnetic actuator, piezoelectric actuator, or thermal actuator.

7. The MEMS of claim 1, further comprising a sensor which senses the rate of capacitance change.

8. The MEMS of claim 7 where the rate of capacitance change in measured at the steepest part of the slope to minimize error.

9. The MEMS of claim 1, wherein said sets of plates are immersed, a shear force being created between the surfaces of the moving plates and the liquid, wherein the rate of change of capacitance is related to said shear force.

10. A MEMS in claim 9, further comprising a sensor which senses the rate of capacitance change as an indication of the liquid's viscosity.

11. A MEMS as in claim 1, further comprising an additional sensor for sensing at least one liquid parameter.

12. A MEMS as in claim 11, wherein the additional sensor is selected from
   a group consisting of a dielectric sensor, a temperature sensor, a conductivity sensor, and a pH sensor.

13. A MEMS as in claim 11, wherein the additional sensor is an integrated temperature sensor.

14. A MEMS as in claim 11, wherein the additional sensor is an integrated interdigitated fixed capacitor for electrochemical sensing.

15. A micro-electromechanical system (MEMS) viscosity sensor, comprising:
   a MEMS variable capacitor comprising a plurality of capacitor plates capable of being submerged in a liquid;
   an actuator for placing a driving force on the variable capacitor which causes relative movement between said plates; said movement creating a shear force between each moving plate and said liquid which damps the movement of said plate and increases the capacitor's response time to said force in accordance with the liquid's viscosity; and
   a sensor coupled to the variable capacitor for sensing said response time as an indicator of the liquid's viscosity.

16. The MEMS of claim 15, wherein said sensor indicates the liquid's viscosity in relation to a reference viscosity and a corresponding reference response time.

17. The MEMS of claim 15, wherein said actuator varies the relative overlay between said plates and thus the capacitance of said capacitor, and said sensor senses the change in said capacitance as a function of time to sense said response time.

18. A micro-electromechanical system (MEMS), comprising:
   a substrate;
   a moveable suspension system carried by said substrate;
   a variable comb capacitor having two sets of interdigitated plates;
   a support holding one of said sets of plates stationary with respect to said substrate;
   a connector coupling the other of said sets of plates to move with said suspension system to vary the overlap between said sets of plates, and thus the capacitance of said capacitor, and
   a sensor coupled to sense the rate of change of said capacitance as an indication of viscosity of liquid in which the capacitor is immersed.

19. The MEMS of claim 18, further comprising a drive actuator, coupled to move at least one of said sets of interdigitated plates parallel to the other interdigitated sets of plates to vary said overlap.

20. The MEMS of claim 19 wherein the drive actuator is a Lorentz actuator.

21. The MEMS of claim 19, wherein the drive actuator is an electrostatic actuator.

22. A method for measuring viscosity of a liquid having a viscosity value using a MEMS device having a variable capacitor, the variable capacitor comprising a plurality of plates, the plates being configured to interleave, a drive actuator and a sensor, wherein the rate of change in the capacitance between the capacitor plates allow the sensing of the viscosity value of the liquid, comprising the steps of:
   submerging at least a portion of the MEMS device into the liquid;
   applying, from the drive actuator, a driving force to said variable capacitor, the application of the driving force causing relative movement between said plates such that at least a portion of the plates overlap, the overlap of said plates causing a rate of change of capacitance, said movement creating a shear force between each moving plate and said liquid, said shear force damping the movement of said plate;
   sensing said rate of change of capacitance; and
   determining said viscosity value, wherein said viscosity value corresponds to said capacitance change.

23. A method as claimed in claim 22 said liquid being replaceable, further comprising:
   comparing the viscosity value to a reference viscosity value; and
   determining whether said liquid should be replaced.

24. A method as claimed in claim 22, wherein said plates have a response time for
   responding to said driving force, further comprising sensing said response time of said plates as an indicator of the viscosity value.

* * * * *